(12) United States Patent
Doak

(10) Patent No.: US 10,561,547 B2
(45) Date of Patent: Feb. 18, 2020

(54) MULTI-PURPOSE LITTER CLAMP AND ATTACHMENTS

(71) Applicant: Morzine Medical LLC, Atlanta, GA (US)

(72) Inventor: John H. Doak, Baltimore, MD (US)

(73) Assignee: Morzine Medical, LLC, Atlanta, GA (US)

( * ) Notice: Subject to any disclaimer, the term of this patent is extended or adjusted under 35 U.S.C. 154(b) by 42 days.

(21) Appl. No.: 15/789,294

(22) Filed: Oct. 20, 2017

(65) Prior Publication Data

US 2018/0110662 A1 Apr. 26, 2018

Related U.S. Application Data

(60) Provisional application No. 62/410,467, filed on Oct. 20, 2016.

(51) Int. Cl.
| | |
|---|---|
| A61G 1/04 | (2006.01) |
| F16M 13/02 | (2006.01) |
| A61G 1/052 | (2006.01) |
| A61B 90/57 | (2016.01) |
| F16B 2/12 | (2006.01) |

(52) U.S. Cl.
CPC ............... *A61G 1/04* (2013.01); *A61B 90/57* (2016.02); *A61G 1/052* (2013.01); *F16M 13/022* (2013.01); *A61B 2090/571* (2016.02); *A61G 2203/78* (2013.01); *F16B 2/12* (2013.01)

(58) Field of Classification Search
USPC .............. 248/229.22, 229.24, 229.2, 229.12, 248/229.14; 269/87, 86, 95, 136, 140, 269/143, 147, 149, 271
See application file for complete search history.

(56) References Cited

U.S. PATENT DOCUMENTS

| | | | | | |
|---|---|---|---|---|---|
| 3,993,279 | A | * | 11/1976 | Holt ........................ | E04G 17/18 248/235 |
| 5,558,261 | A | * | 9/1996 | Hedeen ..................... | B60R 9/10 224/42.13 |
| 5,582,377 | A | * | 12/1996 | Quesada ................. | A47F 5/083 24/343 |
| 5,711,397 | A | * | 1/1998 | Flora .................. | A62B 35/0062 182/3 |
| 6,079,678 | A | * | 6/2000 | Schott ...................... | A61G 7/05 248/125.1 |
| 6,898,905 | B1 | * | 5/2005 | Kirschner ............... | F16B 2/065 248/228.5 |
| 8,403,280 | B2 | * | 3/2013 | Halverson ................ | H04R 1/08 248/228.5 |

(Continued)

Primary Examiner — Alfred J Wujciak
(74) Attorney, Agent, or Firm — Stephen J. Stark; Miller & Martin PLLC

(57) ABSTRACT

A multi-purpose litter clamp comprises a clamp that preferably spans below the litter connecting to opposing longitudinal litter poles on opposite sides of the litter. The clamp can attach rigidly and securely to both sides of the litter. In many embodiments, all but a few inches of the litter's longitudinal poles are covered with a nylon fabric that make up the 'bed' of the litter. A plurality of clamp accessories can facilitate rapid and effective attachment and/or removal of medical equipment connected to a patient directly to the litter on which the patient lies, either during transport and/or while in a field hospital.

7 Claims, 11 Drawing Sheets

(56) References Cited

U.S. PATENT DOCUMENTS

| | | | |
|---|---|---|---|
| 9,216,307 B2* | 12/2015 | Liu | E04G 21/32 |
| 10,018,208 B2* | 7/2018 | Hollis | F16B 2/12 |
| 10,128,887 B2* | 11/2018 | Balmer | A45F 5/10 |
| 2011/0016632 A1* | 1/2011 | Hopf | A47B 97/00 |
| | | | 5/503.1 |
| 2015/0157306 A1* | 6/2015 | Schuele | A61B 17/02 |
| | | | 600/227 |
| 2015/0257958 A1* | 9/2015 | Allen | A61G 13/10 |
| | | | 108/49 |
| 2018/0000666 A1* | 1/2018 | Sirkin | A61G 1/04 |

* cited by examiner

MULTI-PURPOSE LITTER CLAMP AND ATTACHMENTS

CLAIM OF PRIORITY

This application claims the benefit of U.S. Provisional Application No. 62/410,467 filed Oct. 20, 2016, which is incorporated herein by reference in its entirety.

FIELD OF THE INVENTION

The present invention relates to clamps and attachments thereto for use with litters (a.k.a. stretchers) for use in providing medical assistance to wounded soldiers.

BACKGROUND OF THE INVENTION

Badly wounded soldiers, marines, sailors, airmen, and noncombatant civilians are typically carried on a stretcher or "litter" in U.S. military parlance from the point of injury to a place of medical treatment such as a Battalion Aid Station or other field hospital, and then subsequently to a rear-area fully-equipped Base hospital.

While being treated in a field hospital, the patient usually lies on a litter supported on litter stands, which are essentially folding tubular metal sawhorses.

When the patient has been stabilized, he is typically transferred to a major combat theatre hospital such as Bagram Air Base in Afghanistan, and subsequently either to a major regional military hospital such as Ramstein Air Base in Germany, and/or directly to a military hospital in America such the Brooke Army Burn Center in San Antonio, Tex.

Generally depending on the nature and the severity of injury, throughout the above process, the patient lying on the litter is commonly connected to a variety of life-sustaining medical support equipment such as a) one or more gravity-fed intravenous (IV) fluid bags suspended from a hook on an IV pole above the litter; b) an oxygen bottle and valve/regulator; c) a fluid management device that heats refrigerated blood or plasma before infusing it into the patient; d) a ventilator; e) a vital signs monitor; and f) other medical field trauma-care items.

The current problems here are, when the litter bearing the patient moved from one point to another, how to move medical equipment connected to the patient. And further how and where to secure this medical equipment connected to the patient while the patient is on a litter in a field hospital without setting it on the floor if, as often the case, there are no tables or portable stands available to support medical equipment beside the litter.

Out of necessity during transport, connected pieces of medical equipment are often placed on the patient's chest or on the litter between the patient's legs. The medical items connected to the patient can be transported on a cart if available, or can be carried by accompanying medical personnel, but in both cases, there is risk of the equipment being accidentally dislodged.

Regarding IV bags and IV poles, most U.S. military litters have integral mounting holes to support IV poles. However, there are many litters including the so-called "NATO litter" in common use that do not have IV pole mounting holes.

Currently, the only mounting system for securely attaching medical equipment to a litter to my knowledge is the Special Medical Emergency Evacuation Device or "SMEED". This was invented and patented by Staff Sergeant Eric Smeed of the U.S. Army in 2000 as U.S. Pat. No. 6,493,890. It consists of a 14"×22" platform with multiple attachment points, and is designed to be fixed to the litter above the patient's lower legs.

The SMEED's shortcoming are a) it is fairly space-consumptive, bulky, and heavy; and b) it being fixed on the litter above a patient's lower extremities restricts access to the patient's lower extremities; and c), it being fixed on the litter above the patient prevents the patient from being readily taken off the litter without removing it and possibly in the process accidentally dislodging medical equipment connected to the patient.

Thus, there is the need exists for a rapid and effective method of securely attaching and subsequently removing medical equipment connected to a patient directly to the litter on which the patient lies, such that the equipment accompanies the patient and litter both during transport and while in a field hospital.

SUMMARY OF THE INVENTION

It is an object of many embodiments of the present invention to provide a litter clamp having jaws which connect to opposing poles of a litter with a crossbar spanning below a bed of the litter.

It is another object of many embodiments of the present invention to provide a litter clamp which secures to both poles of a litter and provides a plurality of attachment locations for receiving medical equipment and/or accessories to assist in treating a patient on the litter.

It is an object of many embodiments of the present invention to provide a clamp which provides a mount which can possibly receive a bottle holder, possibly in either or both of a horizontal and vertical position.

It is an object of many embodiments of the present invention to provide a clamp which provides a mount which receives an IV pole.

It is an object of many embodiments of the present invention to provide a clamp which provides a mount which receives a tray, the tray preferably being at least one of elevationally adjustable and having a pan or platform mounted to a base whereby the pan/platform structure can slide in our out relative to the base thereby positioning the pan/platform either over a portion of the patient and/or at least partially external to the area above the litter.

While various embodiments can connect to litter poles in different manners, all embodiments have first and second jaws which are received at least partially about the litter poles, respectively. A crossbar connects the jaws and spans a distance below the jaws and the bed of the litter. For many embodiments, outwardly disposed relative to the clamp and jaws are mounts which have at least one, if not a plurality of spaced apart, or even symmetrically disposed attachment locations. A rail can be located outwardly relative to the mount. The attachment locations can be vertically aligned bores which receive a shaft, shank, rod or other structure there through, which for many embodiments can be selectively secured in place with an operator (such as to set at a specific elevation, prevent from rotation, etc.).

Various attachments can attach at the locations including, but not limited to an iv pole, a tray and a bottle holder. These attachment can also potentially provide unique features whether it be a bottle holder that can quickly and/or easily be manipulated to accept bottles/tanks of different height and/or width (i.e., diameter for many bottles), a tray that may be elevationally adjustable and potentially provide a base with at least one of a pan or platform that can be slid relative to the base so that the pan/platform can be moved to be positioned (and then locked) so that it is either more over a patient's body and/or principally externally disposed relative to a patient when on the litter.

Still other embodiments may have these and/or other features.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
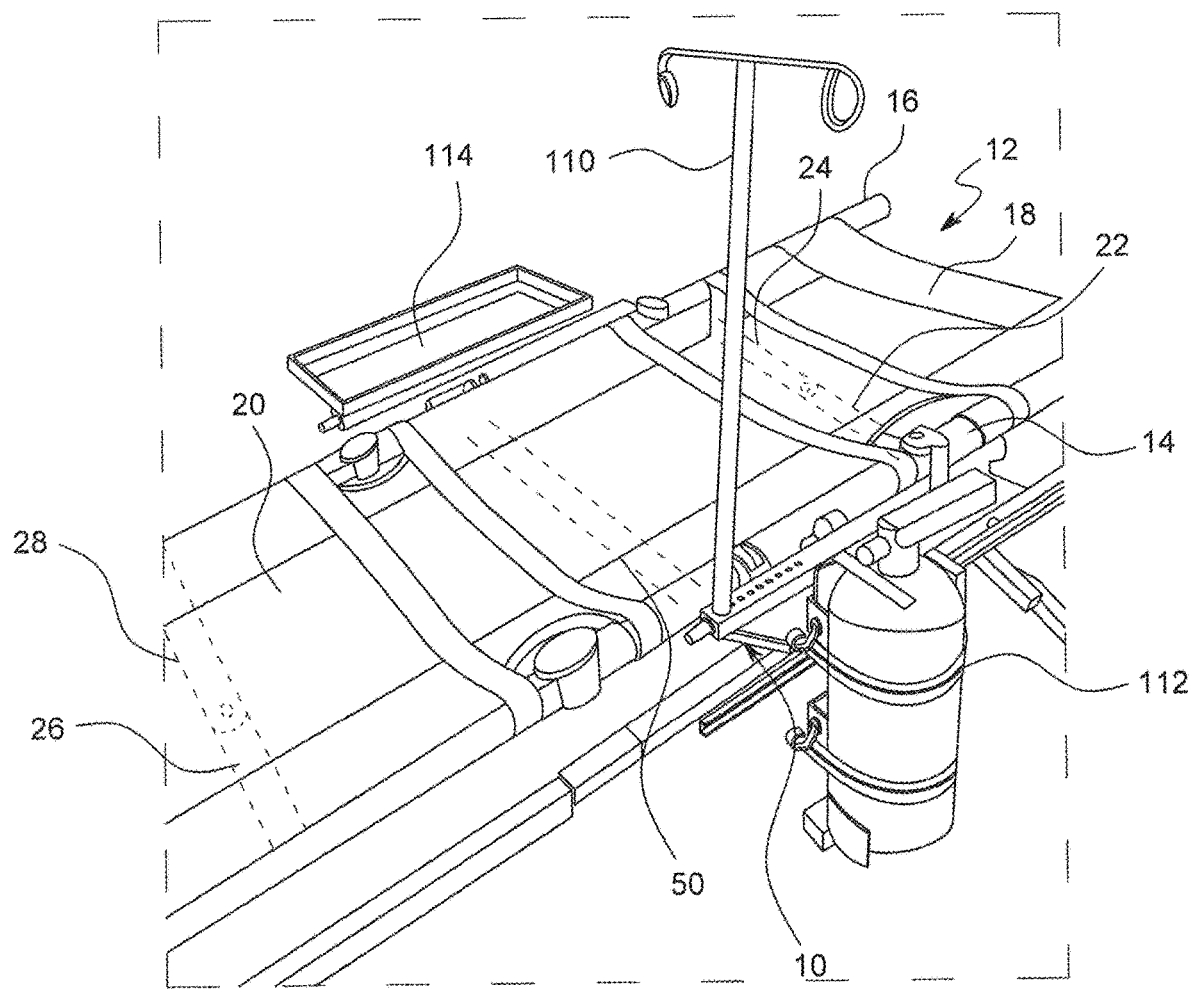
FIG. 1 is a perspective top view of a multi-purpose litter clamp attached to a litter showing accessories assembled to the litter of a presently preferred embodiment of the invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention is directed toward a multi-purpose litter clamp 10, also referred to as a Doak multi-purpose litter clamp, which preferably comprises a clamp 10 that can span across and below a litter 12 to connect onto the opposing longitudinal litter poles 14,16 on opposite sides of the litter 12. There are a number of ways the clamp 10 can connect to the poles 14,16 as will be explained below for various embodiments.

By attaching rigidly and securely to both sides of the litter 12, the clamp 10 can eliminate a problem of clamps that fit just one side of the litter 12 (which may tend to rotate out of position about a litter pole 14,16 and/or suffer other defects). In many embodiments, all but a few inches of the longitudinal poles 14,16 of the litter 12 are covered with a nylon or other fabric 18 that makes up the bed 20 of the litter 12. The fabric 18 is normally stretched tightly between the poles 14,16 in an in-use configuration through the use of struts 22,24 and 26,28 which are normally pivotably connected (so that they can transition between a storage position (not shown) and an in-use configuration illustrated). At ends of the struts 22,24,26,28 below the poles 14,16 are often feet (not shown) which can support the litter 10 above the ground, typically a few inches.

In the absence of a fairly massive and heavy clamping device, prior art single-side litter clamps are prone to 'drooping' or rotating on the litter pole's nylon fabric covering from the weight of the medical equipment, and consequently not rigidly secured to the litter.

Figure 2:
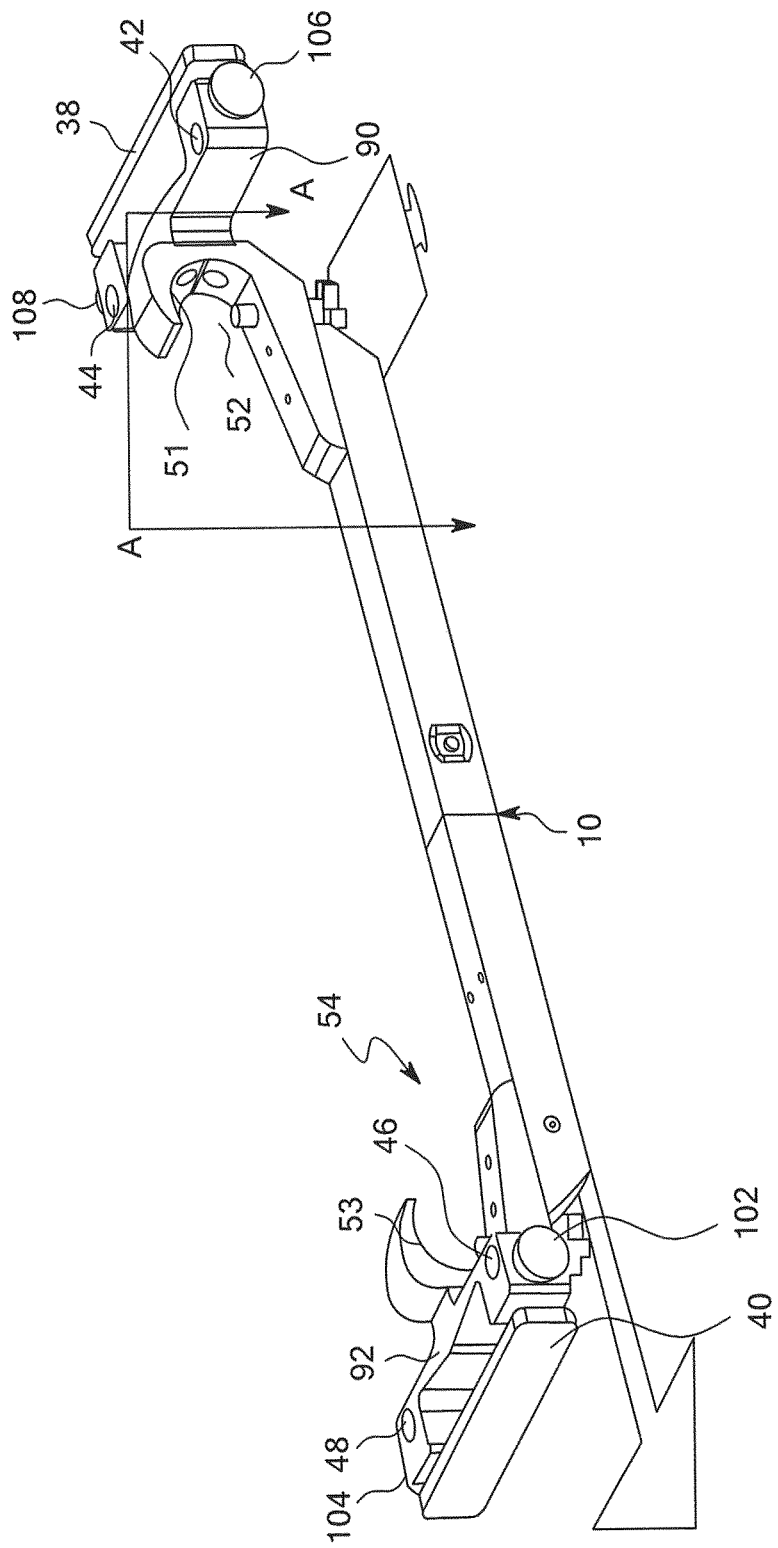
FIG. 2 is a perspective top view of a multi-purpose litter clamp of a first alternative embodiment, but similar to FIG. 1, unattached from the litter shown in FIG. 1.

As shown in FIG. 1 illustrates an embodiment of the multi-purpose litter clamp 10 attached to the litter 12 with at least one of the illustrated accessories and/or others assembled to the litter 12 and clamp 10 in the form of a bag support or iv pole 110, a tank support or bottle holder 112 with tank 120 attached thereto, and a tray 114. FIG. 2 shows the clamp 10 having rails 38,40 (first and second) externally disposed relative to attachment locations 42,44,46,48 (also to mounts 90,92, jaws 52,54 and/or crossbar 50) which will be discussed in further detail below.

A ¾" square ⅛" wall aluminum tube or other structure may function as a crossbar 50 bridging the two opposing litter longitudinal poles 14,16. On each end of this crossbar 50 (and above) and at least substantially perpendicularly disposed thereto are vertical jaws 52,54 (first and second) operably coupled together with the crossbar 50. Some jaws 52,54 may be approximately 1" wide by 3¾" high, possibly made of aluminum providing a half-moon shaped cutout with a radius cooperating with the longitudinal pole 14,16 and its fabric 18 (which is often covering over much of the poles 14,16). The 'half-moon' cut-outs 51,53 can provide a similar radius (preferably slightly oversized) to cooperate with the diameter of the litter poles 14,16 (and fabric 18 thereabout). This is both to firmly grip the litter poles 14,16 and most important, secure the litter clamp 10 to the litter 12. Jaws 52,54 may be inwardly oriented as shown relative to the crossbar 50 and/or outwardly oriented (not shown).

Figure 3:
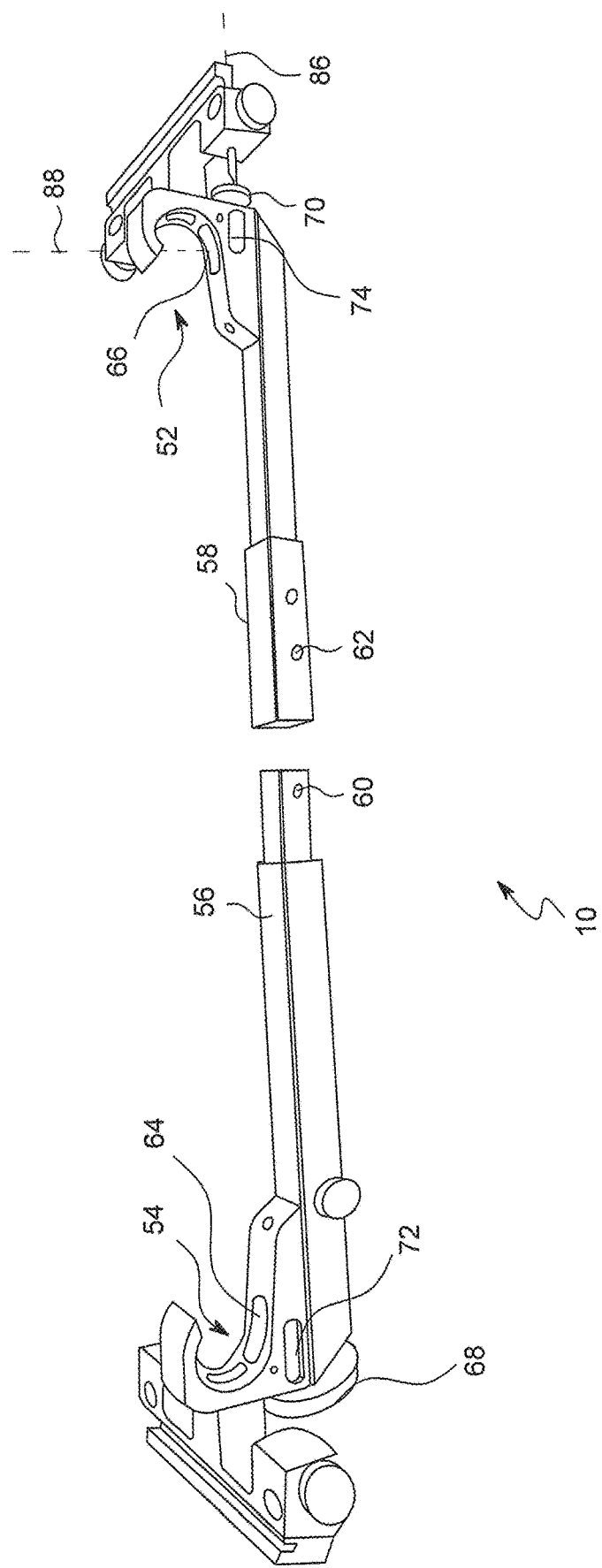
FIG. 3 is a front perspective view of the multi-purpose litter clamp of FIG. 1 in a disassembled configuration.
Figure 4:
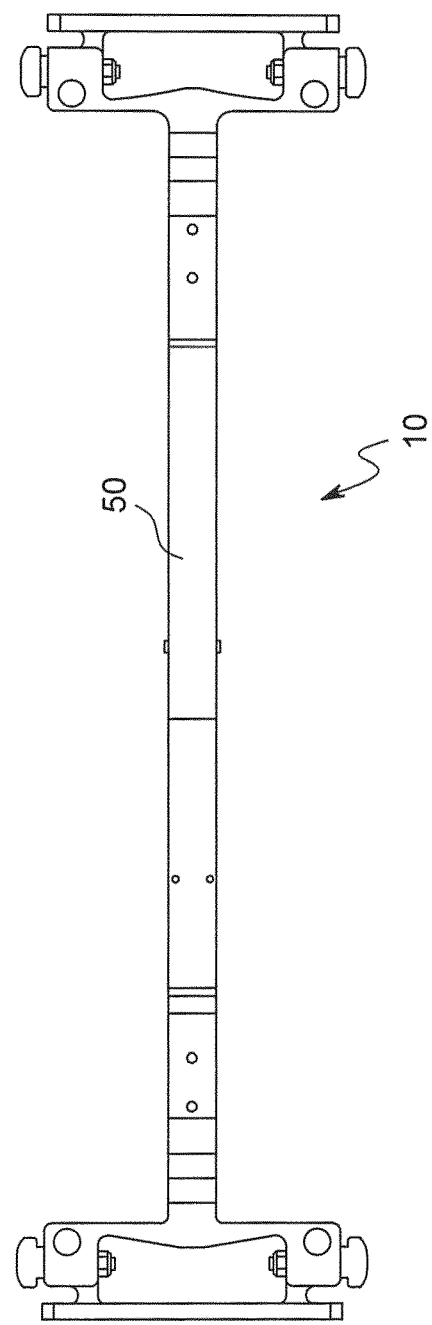
FIG. 4 a top view of the multi-purpose litter clamp of FIGS. 1-3.

As shown in FIG. 3 and others, crossbar 50 may be made of more than one piece, such a two piece 56,58 embodiment shown in FIG. 3. Pieces 56,58 can connect intermediate the jaws 52,54 in an installed configuration with a resiliently biased ball 60 of first piece 56 received in a bore 62 of second piece 58 to provide for a rigid and secure connection when connected, while permitting rapid assembly/disassembly.

The embodiment of FIG. 3 has jaws 52,54 that have thumbs 64,66 respectively which are operably coupled to operators 68,70 respectively which move the thumbs 64,66 into the cutouts of the jaws 52,54 to connect securely to poles 14,16 (and fabric 18 therearound, if present at that location). In this embodiment, the thumbs 64,66 move vertically while the operators 68,70 rotate shafts 72,74 along horizontal axes. The embodiments of FIGS. 2 and FIG. 5 operate differently.

As shown in FIG. 3, the crossbar 50 can be approximately 2" below the contact joint of the jaws 52,54 that clamp on the litter poles 14,16 (jaws 52,54 are illustrated above the crossbar 50 in this embodiment). Many litter stands have a 'dropped' cross bars or struts as described above to provide clearance for the patient's body lying on the litter bed. Without that, the fabric 18 of the litter 12 would often stretch and sag under the weight of the patient's body and create pressure points where the patient's body makes contact through the litter fabric 18 with the crossbar or struts of the litter stand. The dropped crossbar in the litter clamp 10 can meet the same objective. Litter fabric 18 refers to the material making up the bed 20 which is normally a nylon, but could be other material(s) provided as a sheet for other embodiments.

Figure 5:
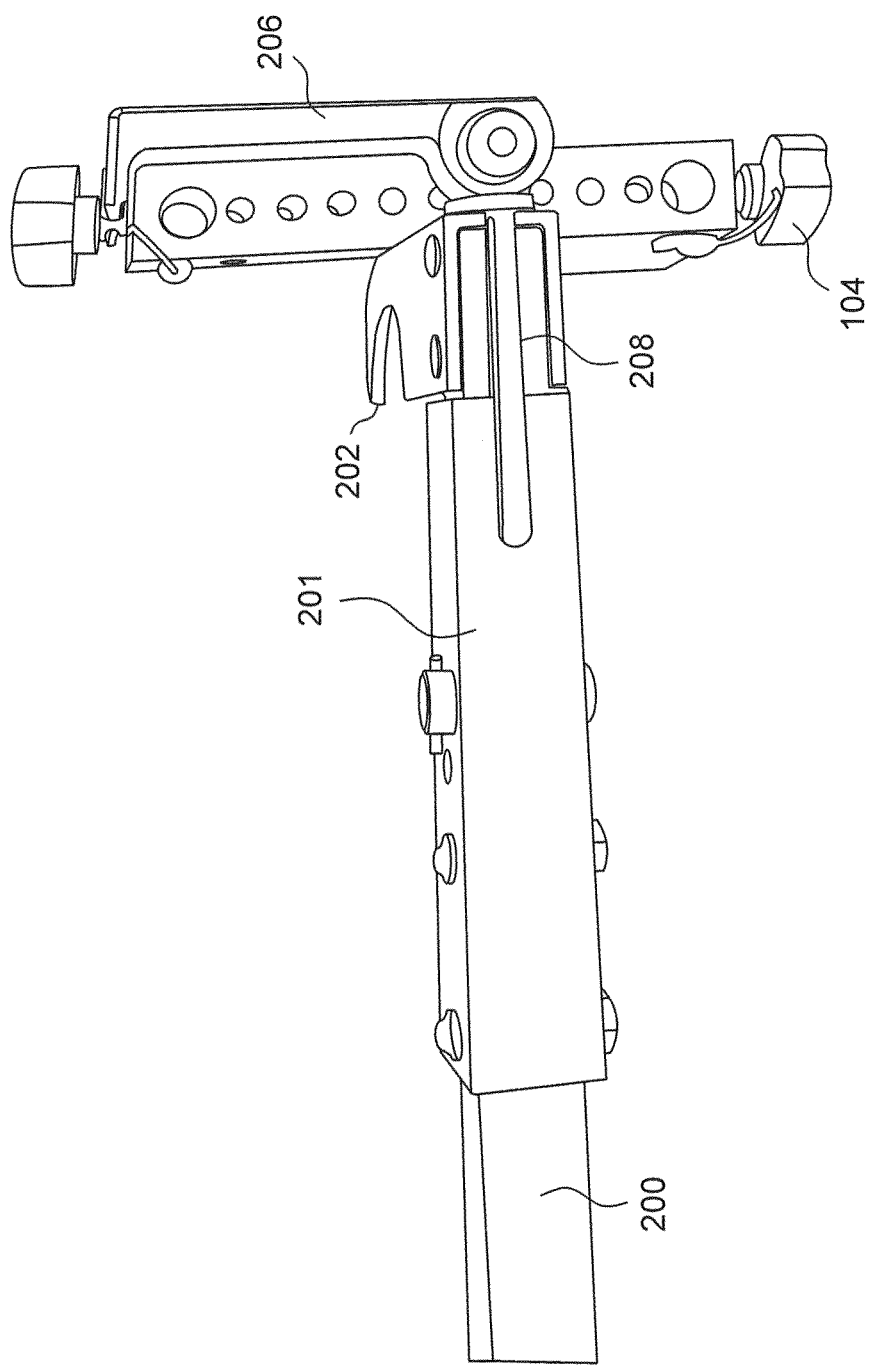
FIG. 5 is a bottom close-up view of a left side of a multi-purpose litter clamp of a second alternatively preferred embodiment showing a cam-action lever handle and a threaded rod without a surgical side rail attached.

For the embodiment shown in FIG. 5, the jaw on one end of the crossbar 200 can be permanently connected, such as riveted or otherwise connected to the crossbar 200. The clamping jaw 202 on the other end of the crossbar 200 can be connected to a sleeve 204 that telescopes over (or into) the cross bar 200. This sleeve 204 with the jaw 202 slides outwardly to fit the clamp 10 over the opposing-side litter poles 14,16, and then slides in to contact both litter poles 14,16.

Inside the sleeve 204 can be a ¼-20 threaded rod 208 (or other structure) fixedly secured inside the crossbar 200. The other end goes through, around and/or beyond the illustrated jaw 202, and can be secured with a swiveling cam-action lever handle 206 or other operator to secure the sleeve 204 in a locked configuration to possibly provide a biasing force of the jaws 202 (the other not shown) toward one another as would be understood by those of ordinary skill in the art. When the litter clamp 10 is fitted over the opposing-side litter poles 14,16 and the sleeve 204 pushed it to take up the slack, turning (or pivoting about pivot 210) the swiveling cam-action lever handle 206 can rigidly compress the jaws 202 relative to each other, and in turn rigidly clamps the jaws 202 (other not shown) to the litter 12. The clamping force on the litter 12 can be so great that it can visibly compress the distance between the opposing-side litter poles 14,16. In the illustrated embodiments, the jaws 52,54 securely connect to the litter poles 14,16 respectively when installed. Spring 99 shown in FIG. 6 may be useful so that the clamps may be spring loaded whether a handle 206 is utilized to providing the clamping action or force, or not. Other spring biasing mechanisms may be utilized to assist in pulling jaws 202 (and 52,54 for some other embodiments) toward one another to connect to litter poles 14,16.

Figure 6:
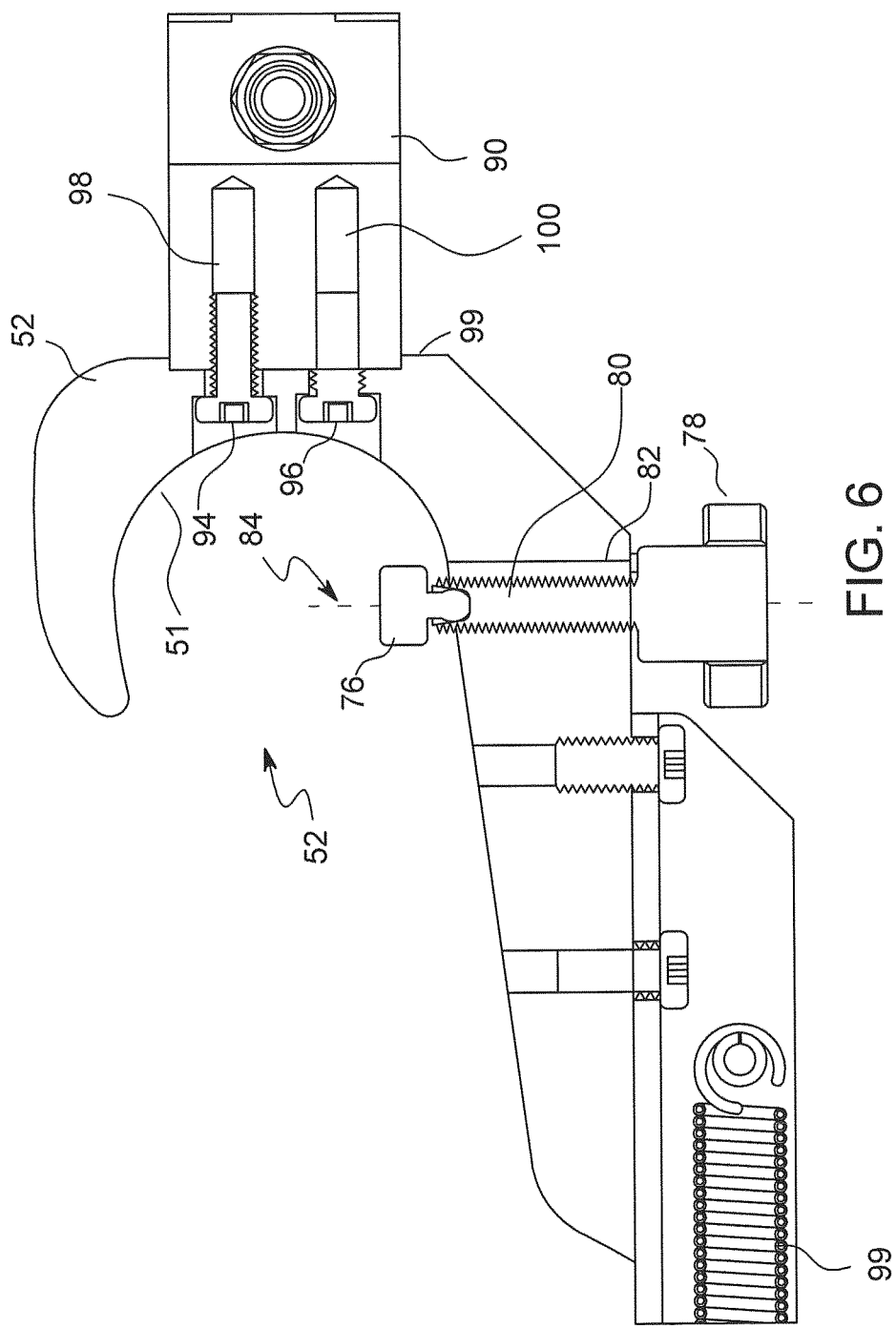
FIG. 6 is a cross sectional view taken along the line A-A of FIG. 2.

FIG. 6 shows an alternately preferred thumb 76 which moves vertically into the first jaw 52 to secure the litter pole 14 or 16 therein. The operator 78 moves threaded rod 80 relative to threads 82 to push the thumb into the cutout of the jaw 52. One difference between FIG. 6 and FIG. 3 is that the thumbs 64,66 and 76 are moved by operators 68,70 vs. 78 oriented in perpendicular directions. The operator 78 moves about the same axis 84 that the thumb 76 moves. Operators like operator 70 rotates about axis 86 which is perpendicular or substantially perpendicular to axis 88 (the direction the thumb 66 moves to secure the jaw 52 to the pole 14 or 16).

Meanwhile, FIG. 6, like FIG. 2 shows mounts 90,92 (first and second mounts 90,92) supporting attachment locations 42,44,46,48 (first, second, third and fourth, respectively) which could be vertically (or otherwise oriented) aligned bores. Mounts 90,92 are connected securely to the jaws 52,54, such as with connectors 94,96 passing through a portion of jaws 52 such as back 99 (opposite cut out 51 to thus be below a litter pole 14,16 when installed) and being securely retained in bores 98,100 of mounts 90,92 as would be understood by those of ordinary skill in the art or otherwise. Mounts 90,92 can connect to optional side rails 38,40 (which may be removable in some embodiments).

In many embodiments, the clamp 10 can within ten seconds or less be attached to the litter 12 and tightened, and provide a rigid and secure mount for various medical equipment to be attached to the litter 12.

Operators such as operators 102,104,106,108 can be used to selectively securely connect to rods or other structures directed into and/or through attachment locations 42,44,46, 48 as would be understood by those of ordinary skill in the art (such as by directing an internal threaded shaft against a rod, turning a cammed shaft against a rod, etc.)

Attachment locations 42,44,46,48 can receive a variety of attachments. FIG. 1 shows an IV pole 110, a bottle holder 112 and a tray 114. Other attachments could be connected in similar or dissimilar manners. Connecting an IV pole 110 having a ½ inch diameter is straightforward for many embodiments. The pole 110 can be received within an attachment location 42,44,46,48 and secured with the appropriate operator 102,104,106,108. With the IV pole 110 connected, any bags supported thereon can be supported by a securely connected pole 110 to the litter 12 so the patient could be moved with the litter 12 to various locations as necessary. Attachment locations 42,44 and/or 46,48 may be symmetrically disposed relative to jaws 52,54 or not for various embodiments.

Operators 102,104,106,108 could be ¼-20 threaded locking thermoplastic knobs with elastomer covers for comfort and nonslip grip. They can be secured with a ¹⁄₁₆" diameter stainless steel wire tether riveted to the tube to prevent the locking knob ever backing out and being lost. Turning the knob clockwise rigidly can secure the IV pole 110 or other pole-mounted device to the mount 90 and in turn the litter 12.

Some mounts 90,92 as shown in at least FIGS. 1 and 5 could have ¼" diameter holes (or other mounting system), such as one inch apart or the top and bottom surfaces in addition to and/or instead of attachment locations 42,44,46, 48. These are for ready attachment points for custom medical equipment brackets to mount whatever present and future medical devices the user employs.

On the outer surface of mounts 90,92 can be bolted or otherwise a ⁵⁄₁₆" thick by 1⅛" high by 6" long aluminum operating table surgical equipment side rail 38 and/or 40, identical to those on the Doak Portable Surgical Table. These rails 38,40 can provide mounting surfaces for any medical or surgical equipment the user has that mounts on a surgical table side rail. The rails 38,40 are preferably outwardly disposed relative to the jaws 52,54 and/or mounts 90,92.

Many embodiments provide a quick-connect and quick-disconnect rigid litter mounting system, that within seconds can be adjusted in tension without tools, for almost any medical device the user employs for wounded patients both in transport and while in field hospitals.

Oxygen bottles or other tanks 120 are commonly put between a patient's legs on the litter when being transported, and often set on the floor when the patient is on a litter and litter stand in a field hospital.

Figure 7:
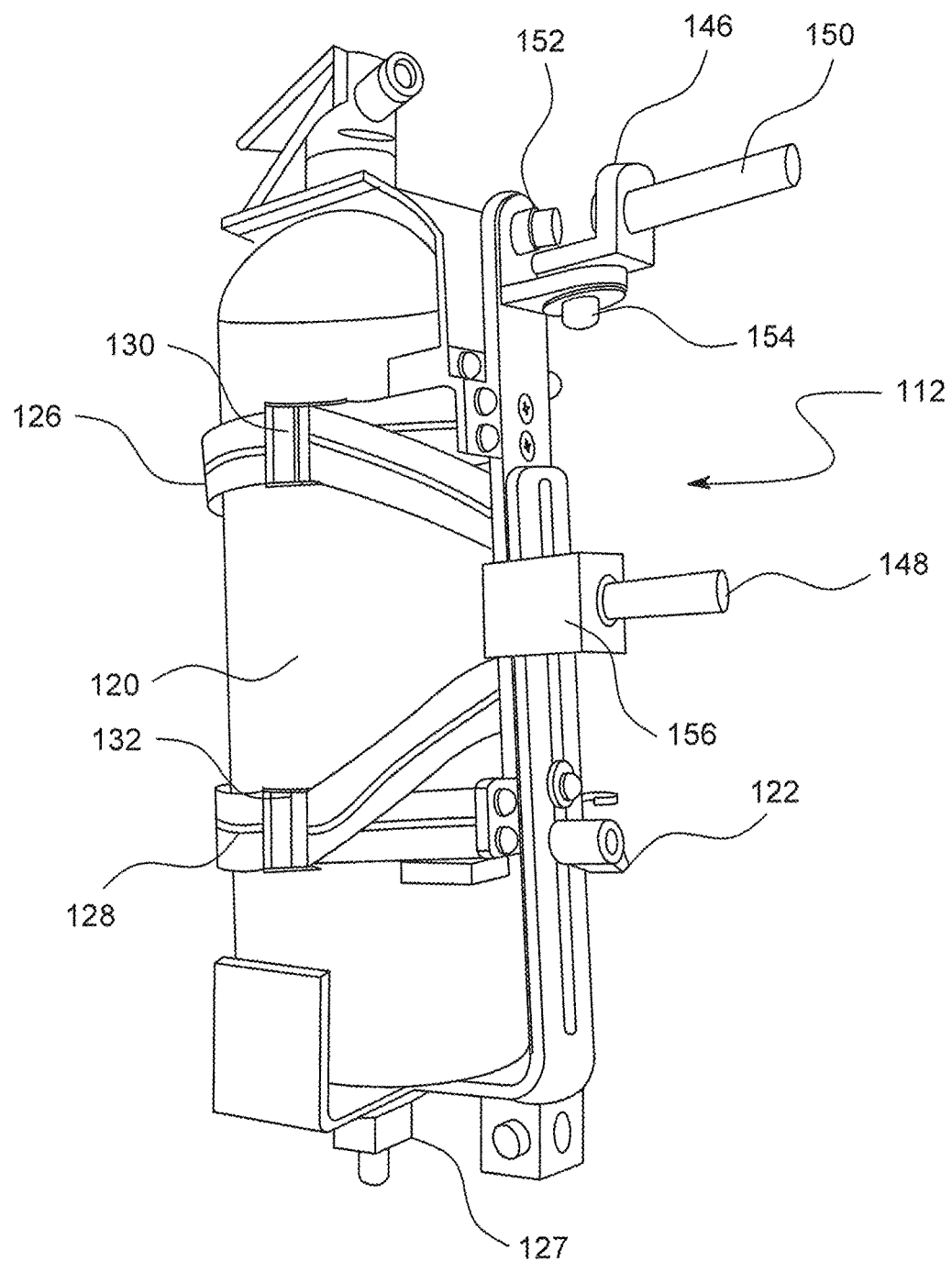
FIG. 7 is a side perspective view of an oxygen bottle holder holding an oxygen bottle removed from the litter shown in FIG. 1.
Figure 8:
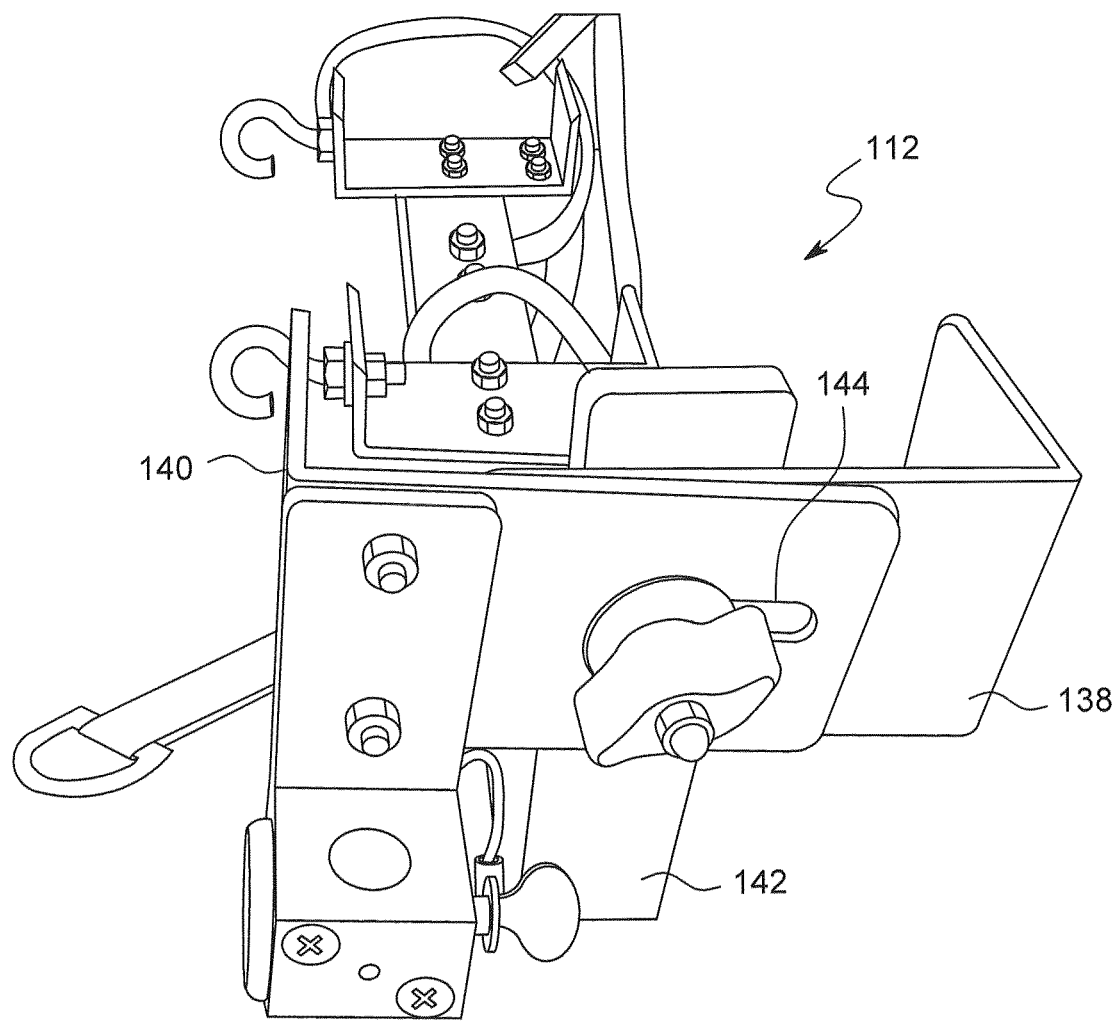
FIG. 8 is a perspective view of the oxygen bottle holder of FIG. 7.
Figure 9:
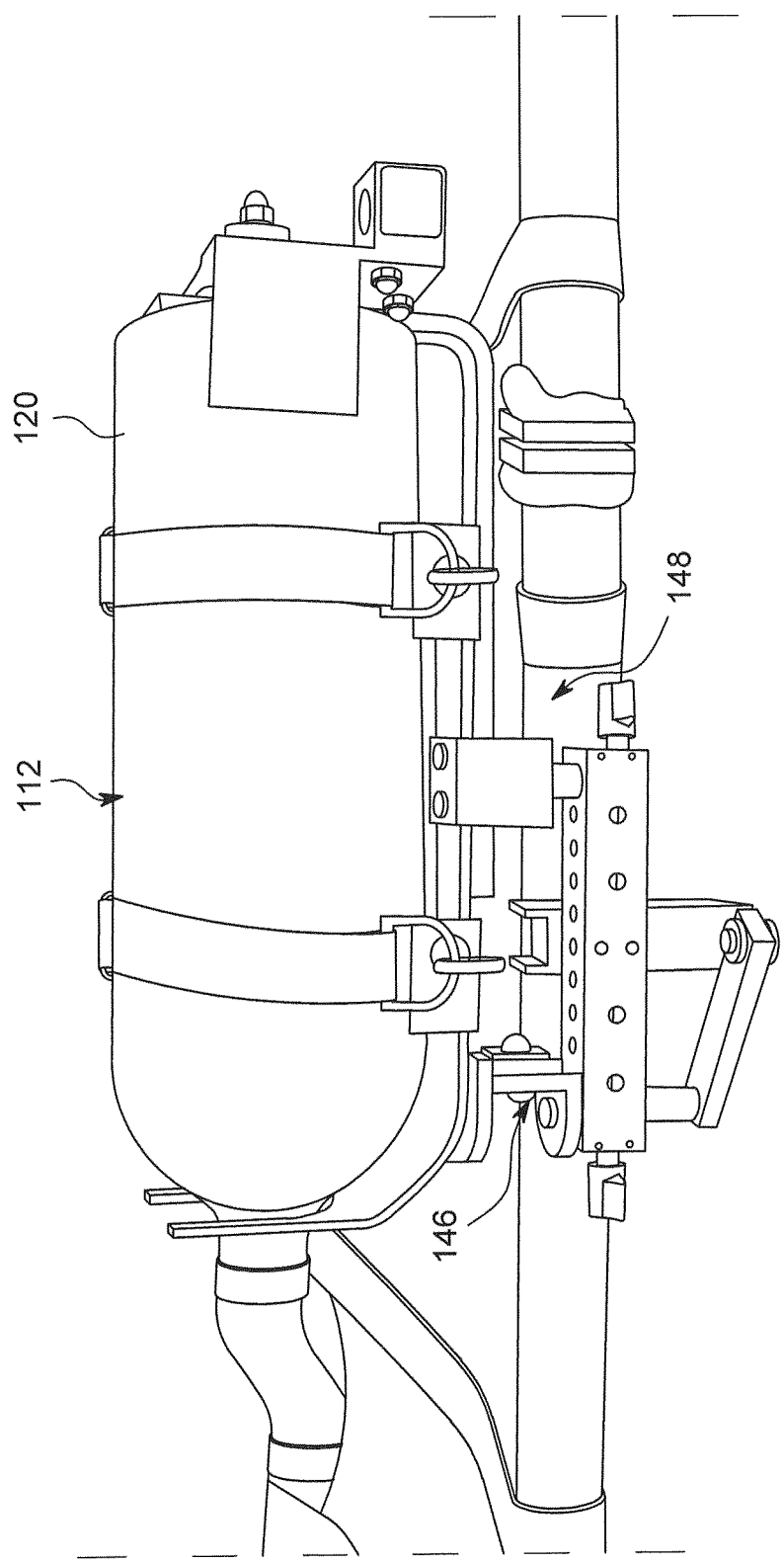
FIG. 9 is a side plan view of the oxygen bottle holder of FIGS. 1, 7 and 8 connected in a different configuration to the litter of FIG. 1.

FIGS. 7-9 showing side views of opposite sides of a bottle holder 112 holding a tank 120 such as an oxygen bottle. The bottle holder 112 can be made from ⅛" and ¼" thick aluminum (or other material) that may be contoured to securely hold oxygen bottles commonly used by the U.S. military in field transport and in field hospitals. It secure oxygen bottles or other tanks 120 both with quick-acting adjusting threaded knobs 122,124 and high-strength straps 126,128 with quick-acting metal adjusters 130,132.

The bottle holder 112 can in just a few seconds or less be mounted in or at one or more of the attachment locations 42,44,46,48 on the litter clamp 10. Gravity alone could hold it in place, or it could also be secured with the threaded knob (operator 102,104,106 or 108).

Since different military medical units use different sizes of oxygen bottle sizes for patient transport, the Bottle Holder 112 can be adjusted, preferably without tools, in a few seconds or less for both different lengths and diameters of commonly used U.S. military oxygen bottles. Specifically, the holder 112 has a back 133 comprised of first and second pieces 134,136 slidingly connected together with at least one piece 134,136 having a slot 138 through which knob 122 can selectively position and secure one piece 134 relative to the other piece 136. A similar or dissimilar construction can be provided for base pieces 138,140 (which also may have slots 144) so that they may be moved in and out relative to foot 142 (which connects to back 133) to accommodate various diameter tanks 120. Knob 124 can secure the base pieces at desired locations to accommodate a particular tank 120.

Meanwhile first and/or second extensions 146,148 can extend from back 133. The first extension 146 could be operably coupled to be directed parallel to the second extension 148 such as illustrated in FIG. 7 and to then be received within two attachment locations 42,44 or 46,48 as illustrated in FIG. 9 to orient the tank 120 horizontally as shown in that figure. First extension could also be positionable such as by rotating post 150 downwardly such as by loosening and then retightening nuts 152,154 so that post 150 extends parallel to (or substantially parallel to) back 133 so that the post can be put in any of the attachment locations 42,44,46,48 such as is sown in FIG. 1. Such a connection optimizes the "real estate" along the poles 14,16 for access and/or other uses. Second extension, if utilized, may be operably coupled to back 133, such as with a slide 156.

The bottle holder can swivel 90 degrees, possibly without tools, in in a few seconds to hold an oxygen bottle or other tank 120 either perpendicular to the ground (vertically) or horizontally, whichever the field medical personnel wish.

Hanging an oxygen bottle vertically occupies the least space alongside the litter 12, and as such minimizes the room taken up by a surgeon or medic working alongside the litter. Mounting the oxygen bottle horizontally facilities stacking litters with patients in medical evacuation or "medevac" vehicles, where litters and patients on certain medevac aircraft can be stacked three high. Also, holding the oxygen bottle horizontally reduces how far the oxygen bottle and holder extends from the side of the litter, to minimize the combined litter/oxygen bottle side-to-side footprint.

Depending on the suitability of the requirement, it observed to find out how much less the oxygen bottle extends from the litter when mounted horizontally than when mounted vertically. The downside is, mounted horizontally, the oxygen bottle takes up much more 'real estate' along the side of the litter, and as such could be in the way of attending medical personnel.

In the field of military field trauma care, transport, and field hospital use, a tray where the medical instruments, medicines and the like to be places other than on the patient or on the ground can be helpful.

One of the Doak Litter Clamp accessories could include an 8" wide by 16" long lightweight aluminum tray (or other tray), possibly with welded corners and double-hemmed 1' high vertical walls for strength to provide a pan 164. It could be designed to hold bandages, antiseptics and medicine, medical instruments, etc., and/or anything that might fit within its 8" by 16" perimeter walls. Other pans or platform configurations can be provided with other embodiments and certainly everything on it need not fit within its perimeter.

Figure 10:
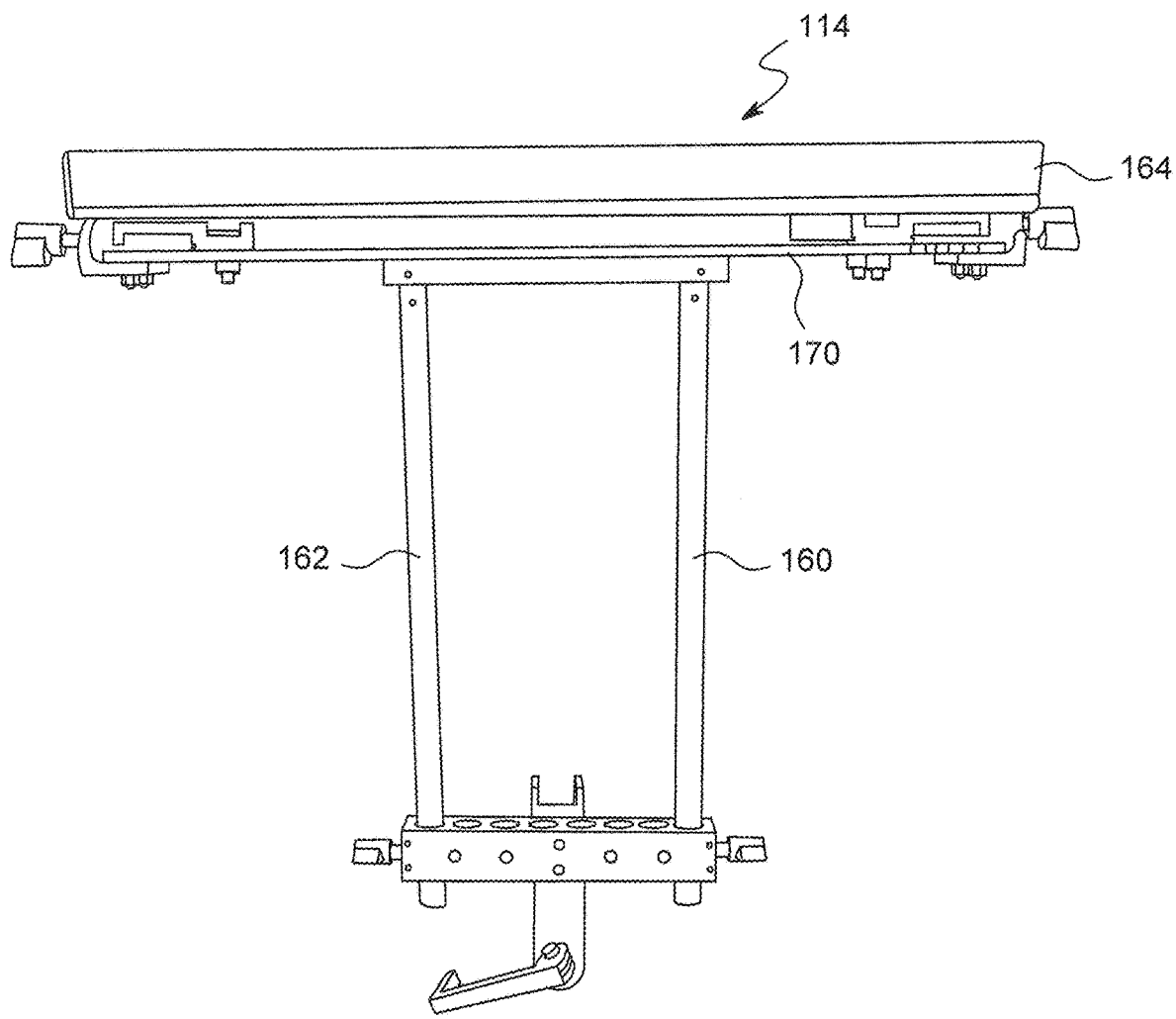
FIG. 10 is a side plan view of the multi-purpose litter clamp attached to the litter showing a tray accessory assembled to the litter as is shown in FIG. 1 in an elevated configuration.
Figure 11:
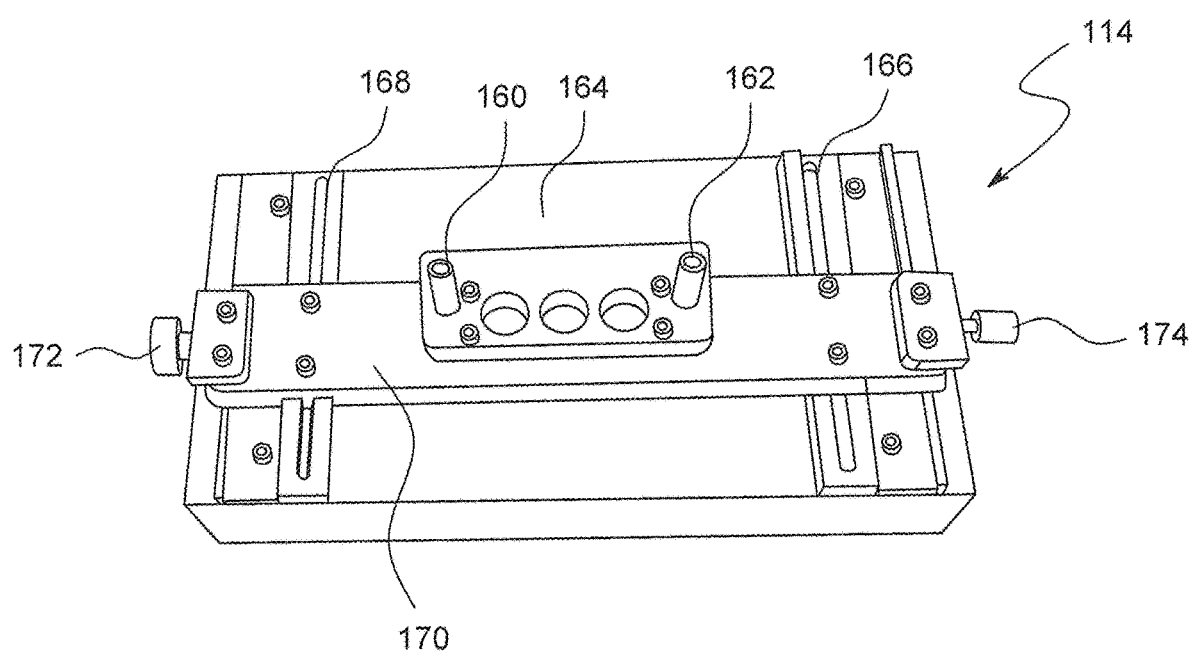
FIG. 11 is a bottom perspective view of the tray of FIGS. 1 and 10.

It has been tested that the exemplary tray 114 can hold 20 pounds without deformation. Other embodiments may behave differently. The tray 114 can mount instantly on the litter clamp 10 attachment locations 42,44,46,48 possibly with permanently-attached ½" diameter supporting stalks 160,162 that fit into the 13 mm holes utilized as attachment locations 42,44,46,48 in a preferred embodiment. These mounting stalks 160,162 can be secured with the operators 102,104,106,108. Stalks 160,162 can be relative long such as shown in FIG. 10 or shorter as shown in FIG. 11. Longer stalks 160,162 may be useful to elevate a platform or pan 164 above a patient. The use of two parallel stalks 160,162 can resist rotation and provide a more stable support than a single stalk alone for at least some embodiments.

Some embodiments provide possibly allow for the pan 164 to slide horizontally or otherwise over a portion of the patient such as by providing slots or slides 166,168 to permit sliding connection of a base 170 (having the stalks 160,162) to the pan 164 so that the pan 164 can be selectively slid to a desired position relative to the base 170 and then secured in position with the operators 172,174.

The pan 164 can be substantially over a portion of a patient on the bed 20 (substantially outwardly directed relative to the illustrated attachment locations 42,44,46,48 to which the pan 164 is connected), or moved to be less and less over the patient, even to the point of being over the attachment locations 42,44,46,48 (and outwardly directed relative thereto). Thus, the pan 164 is slidably and/or horizontally positionable to a selected position relative to the base 170 and the bed 20.

The tray 112 can be provided with ½" diameter threaded aluminum extensions that can be threaded without tools into the fixed mounting stalks 160,162 on the underside of the tray. With these extensions, the tray can be heighted-adjusted to anywhere from 2" to 12" (or other elevation) above the litter. Other constructions may be utilized with other embodiments.

The pan 164 can slide on Teflon spacers to extend either outboard of the litter, or be positioned inboard over the litter if the attending medical personnel so desire.

The sliding tray 114 can be locked in any position inboard or outboard of the litter 12 with a pair of threaded thermoplastic knobs with elastomer covers for comfort and nonslip grip.

FIGS. 1 and 10 are illustrations showing tray 114 mounted on the multi-purpose litter clamp 10 in the outboard position with respect to the litter 12. FIG. 1 shows the tray slid to be outwardly disposed over the rail 16 while FIG. 10 shows the tray possibly over the bed 20.

Sliding the tray 114 inboard over the patient and litter 12 can minimize the outward extension of the tray 114 beyond the side of the litter 12. This can be critical in reducing the side-to-side footprint of the litter 12 during medevac transport.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A litter clamp for connecting to a litter having parallel first and second poles connected by a fabric, said clamp comprising:
   first and second jaws operably coupled together by a crossbar, said jaws located above the crossbar with the jaws securely connectable to both the first and second poles respectively with the crossbar being located below the fabric of the litter;
   a first mount detachable connected to the first jaw providing a first attachment location and a second attachment location; and
   a first attachment is a tray having first and second parallel stalks received in the attachment locations whereby the tray is selectively elevationally adjustable relative to the attachment locations.

2. The litter clamp of claim 1 wherein the crossbar has first and second pieces, each respectively having a length, and the first and second pieces are selectively connected together intermediate the first and second jaws in an installed configuration to provide a crossbar length, and each of the first and second pieces are shorter than the crossbar length.

3. The litter clamp of claim 1 further comprising a second mount connected opposite the second jaw relative to the crossbar, said second mount having third and fourth attachment locations, said attachment locations respectively providing independently operated and selective elevational adjustment at the attachment locations relative to each other.

4. The litter clamp of claim 3 further comprising a bottle holder, said bottle holder received at the third attachment location and having a back comprised of first and second pieces which are slidably disposed relative to one another and selectively set at a desired height for receiving a tank.

5. The litter clamp of claim 3 further comprising a bottle holder, said bottle holder received in the third attachment location and having a base comprised of first and second base sections which are slidably disposed relative to a foot selectively set at a desired width for receiving a tank.

6. The litter claim of claim 1 further comprising a second mount connected to the second jaw opposite the first jaw relative to the crossbar, said second mount having first and second spaced apart attachment locations spaced apart in a longitudinal direction extending perpendicularly to the crossbar and parallel to the first and second poles of the litter, said first and second attachment locations respectively providing independently operated and selective elevational adjustment at the attachment locations relative to each other.

7. The litter clamp of claim 3 further comprising a bottle holder, said bottle holder having an extension cooperating with the third attachment location, said extension selectively positionable in a horizontal and a vertical configuration.

* * * * *